United States Patent
Coppi et al.

(10) Patent No.: US 7,777,044 B2
(45) Date of Patent: Aug. 17, 2010

(54) PROCESS FOR THE PREPARATION OF OPTICALLY ACTIVE DERIVATIVES OF 2-(2-PYRIDYLMETHYLSULFINYL)-BENZIMIDAZOLE VIA INCLUSION COMPLEX WITH 1,1'-BINAPHTHALENE-2,2'DIOL

(75) Inventors: Laura Coppi, Barcelona (ES); Ramón Berenguer Maimó, Barcelona (ES); Yolanda Gasanz Guillén, Barcelona (ES); Jorge Medrano Rupérez, Barcelona (ES)

(73) Assignee: Esteve Quimica, S.A., Barcelona (ES)

( * ) Notice: Subject to any disclaimer, the term of this patent is extended or adjusted under 35 U.S.C. 154(b) by 187 days.

(21) Appl. No.: 11/817,624

(22) PCT Filed: Feb. 22, 2006

(86) PCT No.: PCT/EP2006/060193

§ 371 (c)(1),
(2), (4) Date: Aug. 31, 2007

(87) PCT Pub. No.: WO2006/094904

PCT Pub. Date: Sep. 14, 2006

(65) Prior Publication Data

US 2008/0167473 A1 Jul. 10, 2008

(30) Foreign Application Priority Data

Mar. 3, 2005 (ES) ................. 200500546

(51) Int. Cl.
*C07D 401/12* (2006.01)
(52) U.S. Cl. .................................. 546/273.7
(58) Field of Classification Search ............... 546/273.7
See application file for complete search history.

(56) References Cited

FOREIGN PATENT DOCUMENTS

| CN | 122326 A | 7/1999 |
|---|---|---|
| CN | 1329003 | 1/2002 |
| DE | 4035455 A1 | 5/1992 |
| EP | 652872 A | 12/1994 |
| WO | WO9854171 A1 | 12/1998 |
| WO | WO0044744 A1 | 8/2000 |
| WO | WO0078745 A2 | 12/2000 |
| WO | WO2004/002982 A2 | 1/2004 |
| WO | WO2004013126 A1 | 2/2004 |
| WO | WO2007/013743 A1 | 2/2007 |
| WO | WO2007/074099 A1 | 7/2007 |

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 183-226.*
Yu et al., "Physical characterization of, etc.," PSTT, vol. 1 (3), 118-127 (1998).*
Deng, Jingen et al, "Resolution of Omeprazole by Inclusion Complexation with a Chiral host BINOL"; Chengdu Institute of Organic Chemistry, Chinese Academy of Sciences, received Jan. 11, 2000; accepted Mar. 21, 2000.
Notification of Transmittal of the International Search Report and the Written Opinion of the International Searching Authority, or the Declaration, for PCT/EP2006/060193, Esteve Quimica, S.A., issued Jul. 3, 2006, Federico Bonomelli; with Written Opinion of the International Searching Authority, Traegler-Goeldel, M.

* cited by examiner

*Primary Examiner*—Patricia L Morris
(74) *Attorney, Agent, or Firm*—Peter B. Scull; Kristina M. Kalan; Berenbaum Weinshienk PC

(57) ABSTRACT

Process for the preparation of optically active derivatives of 2-(2-piridylmethylsulfinyl)-benzimidazole, or salts thereof, by resolution of the corresponding racemic derivatives of 2-(2-piridylmethylsulfinyl)-benzimidazole. The resolution is performed through the formation of inclusion complexes with (S)-(−) or (R)-(+)-[1,1'-Binaphthalene]-2,2'-diol in the presence of an amine, followed by the break of the inclusion complex by treatment with an hydroxide of an alkaline metal. The enantiomer of the derivative of 2-(2-piridylmethylsulfinyl)-benzimidazole may be obtained by extractions at a particular pH with a suitable organic solvent. The process allows to perform the resolution with high yields and high optical purity, without using neither toxic solvents nor chromatography.

20 Claims, No Drawings

PROCESS FOR THE PREPARATION OF OPTICALLY ACTIVE DERIVATIVES OF 2-(2-PYRIDYLMETHYLSULFINYL)-BENZIMIDAZOLE VIA INCLUSION COMPLEX WITH 1,1'-BINAPHTHALENE-2,2'DIOL The present invention relates to a process for the preparation of optically active derivatives of 2-(2-piridylmethylsulfinyl)-benzimidazole from racemic derivatives of 2-(2-piridylmethylsulfinyl)-benzimidazole.

BACKGROUND ART

Various derivatives of 2-(2-piridinylmethylsulfinyl)-benzimidazole are known as inhibitors of the proton pump and they are effective on the treatment of gastric ulcer. Omeprazole, 5-methoxy-2-[[(4-methoxy-3,5-dimethyl-2-piridyl)methyl]sulfinyl]-1H-benzimidazole; lansoprazole, 2-[[[3-methyl-4-(2,2,2-trifluoroethoxy)-2-pyridinyl]methyl]sulfinyl]-1H-benzimidazole; pantoprazole, 5-(difluoromethoxy)-2-[[(3,4-dimethoxy-2-pyridinyl)methyl]sulfinyl]-1H-benzimidazole; and rabeprazole, 2-[[[4-(3-methoxypropoxy)-3-methyl-2-pyridinyl]methyl]sulfinyl]-1H-benzimidazole stand out among these compounds. These compounds are sulfoxides with a center of asymmetry on the sulphur atom, therefore they exist in the form of a racemic mixture of two enantiomers.

In the last years, the preparation of the enantiomers of pharmacologically active compounds has shown a growing interest because they can show improved pharmacokinetic and biological properties with regard to the racemic mixture.

Among the known enantiomers of the derivatives of 2-(2-piridinylmethylsulfinyl)-benzimidazole is the Esomeprazole with the formula (I) shown below. It is the (S) enantiomer of the racemic product omeprazole. The S configuration corresponds to the (−)-enantiomer.

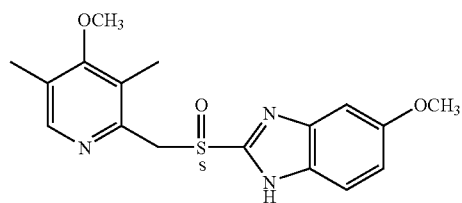
(I)

Several methods for the separation of the enantiomers of omeprazole were described. In DE 4035455, it is described a process of resolution of omeprazole that uses a diastereomeric ether that is separated and later is hydrolised in an acidic solution.

A process for the preparation of the magnesium salt of S-omeprazole based on the resolution of the racemic omeprazole by formation of a diastereomeric ester is described in EP 652.872-A.

The separation of the enantiomers of a prazole that comprises the reaction with an agent of coordination (transition metal), a quelating agent and an organic acid, and the later separation of the resulting diastereomeric adduct is described in WO04/2982-A.

Finally, a resolution process of omeprazole by forming inclusion complexes with bi-2-naphthol, bi-2-phenanthrol or derivatives of tartaric acid is described in CN 1.223.262. The enantiomers are recovered from the inclusion complex by chromatography. An 87% of enantiomeric excess (e.e.) is obtained at the best conditions described in this document, but it requires to use a benzene/hexane mixture as solvent. Benzene is a solvent that has a high toxicity, therefore it is not suitable for working at large scale. With other hydrocarbons such as toluene or xylene, an e.e. lower than 62% is obtained, which would make the process non-viable at industrial scale. This process also shows the typical problems of using chromatography at a large scale. Likewise, the reproduction of the experimental conditions for the preparation of the compounds of interest described in this document shows that, in fact, the products are obtained with low global yield. The same synthetic route is used in Jingen Deng's et al. article, "Resolution of omeprazole by inclusion complexation with a chiral host Binol", *Tetrahedron Asymmetry* 2000, vol. 11, pp. 1729-1732, whose authors are inventors of the patent. Nevertheless, the only solvent described is a benzene/hexane mixture that shows the disadvantages described before.

Therefore, it is of interest the provision of an alternative process for the preparation of each of the individual enantiomers of derivatives of 2-(2-piridinylmethylsulfinyl)-benzimidazole. In particular, if they are easily industrializable and do not involve the use of dangerous solvents nor the separation by chromatographic techniques.

SUMMARY OF THE INVENTION

The objective of the present invention is to provide a process for the preparation of each of the enantiomers of the derivatives of 2-(2-piridinylmethylsulfinyl)-benzimidazole, particularly to obtain each one of the enantiomers of omeprazole, lansoprazole, pantoprazole and rabeprazole. The inventors have found that the resolution of prazoles may be performed in presence of an amine through the formation of inclusion complexes with one of the two enantiomers of a substituted [1,1'-binaphthalene]-2,2'-diol, with high yields and high optical purity, by a process that does not involve the use of dangerous solvents nor chromatographic separation. The enantiomer of the derivative of 2-(2-piridinylmethylsulfinyl)-benzimidazole may be recovered from the inclusion complex by a treatment with a hydroxide of an alkaline metal and extractions at a particular pH with a suitable organic solvent.

Thus, according to an aspect of the present invention, it is provided a process for the preparation of each one of the substantially pure enantiomers of the racemic compound of formula (I), or a salt thereof, as well as its solvates including hydrates,

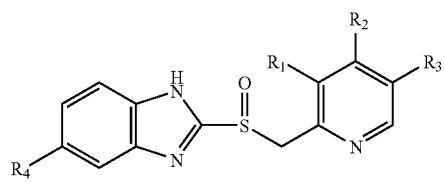
(I)

wherein $R_1$, $R_2$ and $R_3$ are radicals, same or different, which are selected from the group consisting of H; $(C_1$-$C_3)$-alkyl; $(C_1$-$C_3)$-alkoxyl optionally substituted by one or several atoms of fluorine; and $(C_1$-$C_3)$-alkoxy-$(C_1$-$C_3)$-alkoxyl; and $R_4$ is a radical selected from the group consisting of H and $(C_1$-$C_3)$-alcoxyl optionally substituted by one or more atoms of fluorine; which comprises:

a) treating the compound of formula (I) in a racemic mixture form with one of the two enantiomers of a substituted [1,1'-Binaphthalene]-2,2'-diol, in a mixture of an amine and a suitable solvent, in order to separate an inclusion complex formed by one of the enantiomers of the compound of formula (I) with one of the enantiomers of the substituted [1,1'-Binaphthalene]-2,2'-diol;

b) treating the inclusion complex obtained in the previous step with a hydroxide of an alkaline metal in a mixture of water and an organic solvent which is inmiscible or little miscible in water to give one of the enantiomers of the compound of formula (I) in a free base form, or in a salt form thereof; and c) in case of obtaining an enantiomer of the compound of formula (I) in a free base form, optionally, convert it to a salt thereof.

By substantially pure enantiomer is understood the one with an enantiomeric excess enough to a large-scale preparation, what depends on each particular case as those skilled in the art will detect at the moment of the exploitation of the invention. Generally, the process may be useful industrially with at least 95% of enantiomeric excess (e.e.), even if desired it is possible to achieve at least 99% of e.e. through the process of the present invention.

In a preferred embodiment, the substantially pure enantiomer of the compound of formula (I) is that wherein $R_1$ is methyl; $R_2$ is 2,2,2-trifluoroethoxyl; and $R_3$ and $R_4$ are hydrogen. In other preferred embodiments $R_1$ and $R_2$ are methoxyl; $R_3$ is hydrogen; and $R_4$ is difluoromethoxyl. In other preferred embodiment, $R_1$ is methyl; $R_2$ is 3-methoxy-propoxyl; and $R_3$ and $R_4$ are hydrogen. In other preferred embodiment $R_1$ and $R_3$ are methyl; and $R_2$ and $R_4$ are methoxyl.

The strategy used in the resolution of the racemic mixture is based on the formation of inclusion complexes with diastereomic character by addition of a chiral agent. As is already known by the person skilled in the art, diastereomers, unlike enantiomers, have different physical properties, for example solubility, which allows their separation. The selection of the enantiomer of the substituted [1,1'-Binaphthalen]-2,2'-diol to use will be done experimentally to achieve the desired enantiomer of the compound of formula (I).

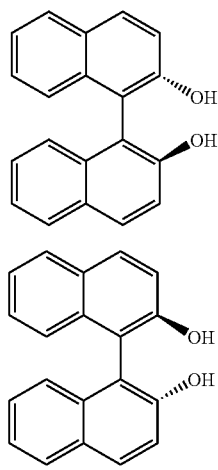

Preferably, the inclusion complex is formed with the (S)-(−)-[1,1'-Binaphthalen]-2,2'-diol of formula (II) or with the (R)-(+)-[1,1'-Binaphthalen]-2,2'-diol of formula (II'), although other substituted [1,1'-Binaphthalen]-2,2'-diols may be used.

Thus, to obtain the S-omeprazole, an inclusion complex is formed by the treatment of omeprazole with the (S)-(−)-[1,1'-Binaphthalen]-2,2'-diol of formula (II). The enantiomeric excess of the complex obtained with S-omeprazole is about 97%.

The most suitable conditions to perform the process vary with the parameters considered by the person skilled in the art, as for example starting materials, temperature and similars. These parameters will be adjusted for every case to achieve the maximum amount of inclusion complex with the derivative of 2-(2-piridylmethylsulfinyl)-benzimidazole. These conditions can be readily determined by said person skilled in the art through routine tests, and with help of the matter taught in the examples of the present description.

Preferably, the molar ratio of the starting materials is 0.5 to 3 mol of the corresponding enantiomer of the [1,1'-binaphthalen]-2,2'-diol per mol of racemic compound. More preferably, the molar ratio ranges from 1.2 to 2 moles of the [1,1'-binaphthalen]-2,2'-diol per mol of racemic compound. The most preferred molar ratio is 1.5 mol of the corresponding [1,1'-binaphthalen]-2,2'-diol per mol of racemic compound.

Preferably, the used solvent is an aromatic hydrocarbon such as toluene or xylene, or a mixture of said aromatic hydrocarbons with an aliphatic hydrocarbon ($C_6$-$C_8$) such as hexane, cyclohexane or heptane. Preferably the solvent is selected from toluene, xylene, toluene/heptane mixtures, toluene/hexane mixtures, xylene/heptane mixtures and xylene/hexane mixtures. The amounts of solvent vary with the starting materials. Usually this amount is comprised between 5 and 50 ml/g. Preferably between 6 and 37 ml/g. More preferably about 12 ml/g.

In a preferred embodiment the amine is a tertiary amine such as triethylamine, tributylamine, and tripropylamine. In a more preferred embodiment, the tertiary amine is triethylamine. The amount of amine varies with the starting materials. Usually this amount is comprised between 0.01 and 5 ml/g. Preferably between 0.1 and 1 ml/g. More preferably about 0.2 ml/g.

Usually, the formation of the inclusion complex is performed at a temperature comprised between 20° C. and the reflux temperature of the solvent used. Preferably at a temperature comprised between 50 and 100° C.

The inclusion complex formed at the first stage can be isolated from the reaction medium by filtration. After the filtration, the inclusion complex is formed by one of the enantiomers of the [1,1'-binaphthalen]-2,2'-diol and one of the enantiomers of the derivative of 2-(2-piridylmethylsulfinyl)-benzimidazole, and the filtrate mainly contains the other enantiomer of the derivative of 2-(2-piridylmethylsulfinyl)-benzimidazole.

One or several recrystallizations of the inclusion complex may be performed, if desired, to increase the e.e. Preferably, it is carried out with an ($C_1$-$C_4$) alcohol, preferably with ethanol, or with one of the solvents used to form the inclusion complex mentioned above.

To obtain the desired enantiomer of the derivative of 2-(2-piridylmethylsulfinyl)-benzimidazole which is a part of the inclusion complex, said inclusion complex must be broken. This break may be performed by a treatment with a hydroxide of an alkaline metal in a mixture of water and an organic solvent that is inmiscible or little miscible in water.

Preferably, the hydroxide of an alkaline metal is sodium hydroxide or potassium hydroxide. More preferably, the hydroxide of an alkaline metal is sodium hydroxide.

Also preferably, the organic solvent that is inmiscible or little miscible in water is selected from aromatic hydrocarbons ($C_6$-$C_8$) such as toluene or xilene; aliphatic chlorides ($C_1$-$C_3$) such as methylene chloride or chloroform, and aliphatic ethers ($C_2$-$C_8$) such as ethyl ether, isopropyl ether or tert-butylmethyl ether.

The amounts of solvent and water vary with the inclusion complex. Usually the amount of solvent is comprised between 1 and 30 ml/g of inclusion complex. Preferably between 6 and 15 ml/g. Likewise, the amount of water is usually comprised between 1-30 ml/g of inclusion complex. Preferably between 4 and 15 ml/g.

Once the complex has been broken, the pH of the reaction medium is adjusted and the phases are separated. Thus, the enantiomer of the used [1,1'-binaphthalen]-2,2'-diol, which is mainly in the organic phase, is separated from the enantiomer of the derivative of 2-(2-piridylmethylsulfinyl)-benzimidazole that remains mainly in the aqueous phase. Preferably the separation is performed at a pH comprised between 10.5 and 12.5. More preferably between 11.0 and 12.0.

The enantiomer of the derivative of 2-(2-piridylmethylsulfinyl)-benzimidazole in a free base form is isolated by extractions of the aqueous phase at a lower pH, preferably between 6-10, with a solvent that is inmiscible or little miscible in water and, optionally, it can be transformed into a salt thereof by conventional methods.

Preferably, the solvent is selected from ($C_6$-$C_8$) aromatic hydrocarbons such as toluene or xilene; ($C_1$-$C_3$) aliphatic chlorides such as methylene chloride or chloroform, and ($C_2$-$C_8$) aliphatic ethers such as ethyl ether, isopropyl ether or tert-butylmethyl ether.

Alternatively, the salt of one of the substantially pure enantiomers of the compound of formula (I) may be obtained directly from the reaction medium by treatment with a salt of an alkaline or alkaline earth metal. In a preferred embodiment, the salt of an alkaline or alkaline earth metal is an halide of an alkaline or alkaline earth metal. In a more preferred embodiment, the halide of an alkaline or alkaline earth metal is the magnesium chloride.

An advantage of the present invention is the fact that this process for the preparation of each of the substantially pure enantiomers of derivatives of 2-(2-piridylmethylsulfinyl)-benzimidazole can provide any of the enantiomers with equal ease. Likewise, the present invention provides a brief and efficient process for the preparation of the enantiomers of derivatives of 2-(2-piridylmethylsulfinyl)-benzimidazole, with high yields and high optical purity. Furthermore, the enantiomer with opposite absolute configuration could be racemized, what would allow recycling it through the fabrication process and would avoid loosing starting material. Likewise, the resolution agent can be recovered from the organic phase and it can be used in the next fabrication.

Throughout the description and claims the word "comprise" and variations of the word are not intended to exclude other technical features, additives, components, or steps. The content of the abstract of the present application is incorporated herein as reference. Additional objects, advantages and features of the invention will become apparent to those skilled in the art upon examination of the description or may be learned by practice of the invention. The following examples are provided by way of illustration, and is not intended to be limiting of the present invention.

EXAMPLES

The following non-limitative examples illustrate the invention for a particular stereoisomeric configuration. When other configuration of the stereoisomers is required, the invention may be performed on a similar manner starting from the compounds with the suitable configuration, as is obvious to the person skilled in the art.

Example 1

Preparation of the S-omeprazole*(S)-[1,1'-binaphthalen]-2,2'-diol inclusion complex in toluene/heptane with triethylamine 10.0 g of omeprazole (29.0 mmol) and 12.4 g of (S)-(−)-[1,1'-binaphthalen]-2,2'-diol (43.4 mmol) were suspended in 96 ml of toluene, 24 ml of heptane and 2 ml of triethylamine. It was heated at 70° C. for 30 min. It was cooled at 0-5° C., the suspending solid was filtered and dried in vacuo at 40° C. S-omeprazole*(S)-[1,1'-binaphthalen]-2,2'-diol inclusion complex with 1:1 stoichiometric ratio was obtained with a 94% yield (corrected by HPLC) and a 97% e.e. (according to HPLC). 1H-RMN (400 MHz, $CDCl_3$): δ 11.9 (1H, wide signal), 7.96 (1H, s), 7.86 (2H, d, J=8.9 Hz), 7.82 (2H, d, J=8.0 Hz), 7.51 (1H, wide signal), 7.32 (4H, m), 7.25 (2H, t, J=8.0 Hz), 7.14 (2H, d, J=8.3 Hz), 6.89 (1H, d, J=8.5 Hz), 6.79 (1H, wide signal), 4.70 (1H, d, J=13.6 Hz), 4.63 (1H, d, J=13.6 Hz), 3.80 (3H, s), 3.67 (3H, s), 2.17 (6H, s).

Comparative Example 1

Preparation of the inclusion complex S-omeprazole*(S)-[1,1'-binaphthalen]-2,2'-diol in benzene/hexane without amine For comparative purposes S-omeprazole*(S)-[1,1'-binaphthalen]-2,2'-diol inclusion complex was prepared without triethylamine. 1.0 g of omeprazole (2.9 mmol) and 1.2 g of (S)-(−)-[1,1'-binaphthalen]-2,2'-diol (4.3 mmol) were suspended in 29 ml of benzene and 7 ml of hexane. It was heated at 90° C. for 30 min. It was cooled at 0/5° C. The suspending solid was filtered and dried in vacuo at 40° C. 1.5 g of the compound of the title was obtained with a 76% yield corrected by HPLC and a 61% e.e. according to HPLC.

Comparative Example 2

Preparation of the inclusion complex S-omeprazole*(S)-[1,1'-binaphthalen]-2,2'-diol in toluene/heptane without amine 20.0 g of omeprazole (57.9 mmol) and 25.0 g of (S)-(−)-[1,1'-binaphthalen]-2,2'-diol (86.8 mmol) were suspended in 600 ml of toluene and 150 ml of heptane. It was heated at 85° C. for 30 min. It was cooled at 0-5° C., the suspending solid was filtered and dried in vacuo at 40° C. S-omeprazole*(S)-[1,1'-Binaphthalen]-2,2'-diol inclusion complex with 1:1 stoichiometric ratio was obtained with a 25% yield corrected by HPLC and a 94% e.e. according to HPLC.

Example 2

Preparation of the Inclusion Complex S-omeprazole*(S)-[1,1-Binaphthalen]-2,2'-diol in toluene with triethylamine 10.0 g of omeprazole (29.0 mmol) and 12.4 g of (S)-(−)-[1,1'-Binaphthalen]-2,2'-diol (43.4 mmol) were suspended in 80 ml of toluene and 2 ml of triethylamine. It was heated at 70° C. for 30 min. It was cooled at 0-5° C., the suspending solid was filtered and dried in vacuo at 40° C. S-omeprazole*(S)-[1,1'-Binaphthalen]-2,2'-diol inclusion complex with 1:1 stoichiometric ratio was obtained with a 89% yield corrected by HPLC and a 97% e.e. according to HPLC. $^1$H-RMN (400 MHz, CDCl$_3$): δ 11.9 (1H, wide signal), 7.96 (1H, s), 7.86 (2H, d, J=8.9 Hz), 7.82 (2H, d, J=8.0 Hz), 7.51 (1H, wide signal), 7.32 (4H, m), 7.25 (2H, t, J=8.0 Hz), 7.14 (2H, d, J=8.3 Hz), 6.89 (1H, d, J=8.5 Hz), 6.79 (1H, wide signal), 4.70 (1H, d, J=13.6 Hz), 4.63 (1H, d, J=13.6 Hz), 3.80 (3H, s), 3.67 (3H, s), 2.17 (6H, s).

Example 3

Recrystallization of the S-omeprazole*(S)-[1,1'-Binaphthalen]-2,2'-diol inclusion complex in ethanol 5.0 g of the S-omeprazole.(S)-[1,1'-Binaphthalen]-2,2'-diol inclusion complex (e.e. 95.7%) were suspended in 95 ml of ethanol. It was heated at 70° C. until the complete dissolution of the product. Next, It was cooled at 0° C. The crystallized solid was filtered, washed with ethanol and dried in vacuo at 40° C. 3.1 g (62% yield) of S-omeprazole*(S)-[1,1'-Binaphthalen]-2,2'-diol inclusion complex were obtained with a 99.7% e.e.

The crystallization was also performed, with similar results, in the following solvents: methanol and isopropanol.

Example 4

Preparation of Esomeprazole Starting from the S-omeprazole*(S)-[1,1'-Binaphthalen]-2,2'-diol complex in toluene 5.0 g of S-omeprazole*(S)-[1,1'-Binaphthalen]-2,2'-diol complex were dissolved in a H$_2$O/toluene mixture by addition of NaOH 10%. The pH was adjusted to 11.5-12.0 and the organic phase was separated. The process was repeated until it was verified that no (S)-(-)-[1,1'-Binaphthalen]-2,2'-diol remained into the aqueous phase. The pH of the aqueous phase was adjusted to 7.0-7.5 and it was extracted with CH$_2$Cl$_2$. The organic phase was separated, evaporated until dryness and 2.7 g of esomeprazole (yield 99%) were obtained. $^1$H RMN (400 MHz, CDCl$_3$): δ 12.2 (1H, wide signal), 8.18 (1H, s), 7.3-7.7 (1H, wide signal), 6.7-7.2 (1H, wide signal), 6.92 (1H, dd, J=8.9 Hz, J'=2.1 Hz), 4.80 (1H, d, J=13.6 Hz), 4.74 (1H, d, J=13.6 Hz), 3.83 (3H, s), 3.67 (3H, s), 2.23 (3H, s), 2.20 (3H, s).

Example 5

Preparation of Esomeprazole Starting from the S-omeprazole*(S)-[1,1'-Binaphthalen]-2,2'-diol complex in methylene chloride 1.0 g of S-omeprazole*(S)-[1,1'-Binaphthalen]-2,2'-diol complex was dissolved in a water/methylene chloride mixture by addition of NaOH 10%. The pH was adjusted to 11.5-12.0 and the organic phase was separated. The pH of the aqueous phase was adjusted to 7.0-7.5 and it was extracted with CH$_2$Cl$_2$. The organic phase was separated, evaporated until dryness and 0.5 g of esomeprazole (yield 92%) were obtained.

Example 6

Preparation of Esomeprazole Starting from the S-omeprazole*(S)-[1,1'-Binaphthalen]-2,2'-diol complex in tert-butylmethyl ether 5.0 g of the S-omeprazole*(S)-[1,1'-Binaphthalen]-2,2'-diol complex prepared in Example 1, were dissolved in a water/tert-butylmethyl ether mixture by addition of NaOH 10%. The pH was adjusted to 11.3 and the organic phase was separated. The pH of the aqueous phase was adjusted to 7.3 and it was extracted with dichloromethane. The organic phase was separated, evaporated until dryness and 2.7 g of esomeprazole (yield 99%) were obtained.

Example 7

Preparation of Magnesium Esomeprazole Starting from the S-omeprazole*(S)-[1,1'-Binaphthalen]-2,2'-diol complex in toluene 10.0 g of the S-omeprazole*(S)-[1,1'-Binaphthalen]-2,2'-diol complex were dissolved in a water/toluene mixture by addition of NaOH 10%. The pH was adjusted to 11.5-12.0 and the organic phase was separated. The process was repeated until it was verified that no (S)-(-)-[1,1'-Binaphthalen]-2,2'-diol remained into the aqueous phase. 70 ml of H$_2$O were added to the aqueous phase and the pH was adjusted to 11.5-12.0. 1.6 g of MgCl$_2$.6.H$_2$O were added dissolved in 10 ml of H$_2$O. The precipitated solid was filtered, washed with H$_2$O and 4.3 g of magnesium salt of esomeprazole were obtained (yield 76%).

The invention claimed is:

1. A process for the preparation of a substantially pure enantiomer of the racemic compound of formula (I), or a salt thereof,

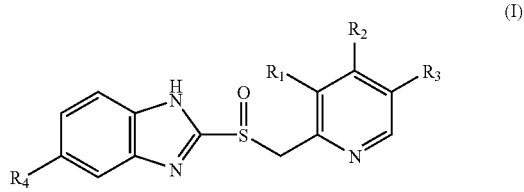

(I)

wherein R$_1$, R$_2$ and R$_3$ are radicals, same or different, selected from the group consisting of H; (C$_1$-C$_3$)-alkyl; (C$_1$-C$_3$)-alkoxyl optionally substituted by one or more atoms of fluorine; and (C$_1$-C$_3$)-alkoxy-(C$_1$-C$_3$)-alkoxyl; and R$_4$ is a radical selected from the group consisting of H and (C$_1$-C$_3$)-alkoxyl optionally substituted by one or more atoms of fluorine; comprising the operations of:

a) treating the compound of formula (I) in a racemic mixture form with one of the two enantiomers of a substituted [1,1'-binaphthalene]-2,2'-diol, in a mixture of an amine and a solvent, in order to separate an inclusion complex formed by one of the enantiomers of the compound of formula (I) with one of the enantiomers of a substituted [1,1'-binaphthalene]-2,2'-diol;

b) treating the resulting inclusion complex with a hydroxide of an alkaline metal in a mixture of water and an organic solvent that is immiscible or minimally miscible in water to give one of the enantiomers of the compound of formula (I) in a free base form, or as a salt thereof; and c) when obtaining an enantiomer of the compound of formula (I) in a free base form, optionally transforming it to a salt.

2. The process according to claim 1, wherein the enantiomer of the substituted [1,1'-Binaphthalene]-2,2'-diol is selected from (S)-(-)-[1,1'-Binaphthalene]-2,2'-diol of formula (II) and (R)-(+)-[1,1'-Binaphthalene]-2,2'-diol of formula (II').

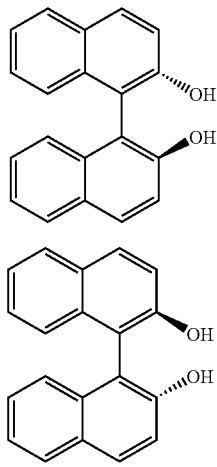

3. The preparation process according to claim 2, wherein $R_1$ is methyl; $R_2$ is 2,2,2-trifluoroethoxyl; and $R_3$ and $R_4$ are hydrogen.

4. The preparation process according to claim 2, wherein $R_1$ and $R_2$ are methoxyl; $R_3$ is hydrogen; and $R_4$ is difluoromethoxyl.

5. The preparation process according to claim 2, wherein $R_1$ is methyl; $R_2$ is 3-methoxy-propoxyl; and $R_3$ and $R_4$ are hydrogen.

6. The preparation process according to claim 2, wherein $R_1$ and $R_3$ are methyl; and $R_2$ and $R_4$ are methoxyl.

7. The preparation process defined in claim 6, wherein the inclusion complex is formed with the (S)-(−)-[1,1'-Binaphthalene]-2,2'-diol of formula (II).

8. The preparation process according to claim 1, wherein the amine of operation a) is a tertiary amine.

9. The preparation process according to claim 8, wherein the tertiary amine is triethylamine.

10. The preparation process according to claim 1, wherein the solvent is an aromatic hydrocarbon selected from toluene and xylene; or a mixture of an aromatic hydrocarbon selected from toluene and xylene with an ($C_6$-$C_8$) aliphatic hydrocarbon selected from hexane, cyclohexane and heptane.

11. The preparation process according to claim 1, further comprising performing one or more selective crystallisations of the inclusion complex in a solvent.

12. The preparation process according to claim 11, wherein the solvent is selected from the group consisting of a ($C_1$-$C_4$) alcohol; an aromatic hydrocarbon selected from toluene and xylene; and a mixture of an aromatic hydrocarbon selected from toluene and xylene with a ($C_6$-$C_8$) aliphatic hydrocarbon selected from the group consisting of hexane, cyclohexane and heptane.

13. The preparation process according to claim 1, wherein the hydroxide of an alkaline metal of operation b) is selected from sodium hydroxide and potassium hydroxide.

14. The preparation process according to claim 13, wherein the hydroxide of an alkaline metal is sodium hydroxide.

15. The preparation process according to claim 1, wherein the organic solvent of operation b) is selected from the group consisting of ($C_6$-$C_8$) aromatic hydrocarbons, ($C_1$-$C_3$) aliphatic chlorides and ($C_2$-$C_8$) aliphatic ethers.

16. The preparation process according to claim 1, wherein the preparation of one of the enantiomers of the compound (I) in a free base form comprises the operations of separating the organic phase at a pH of between about 10.5 and about 12.5, extracting of the aqueous phase at a pH of between about 6 and about 10 with a solvent and, optionally, transforming the resulting compound into a salt thereof.

17. The preparation process according to claim 16, wherein the solvent of the extraction is selected from ($C_6$-$C_8$) aromatic hydrocarbons, ($C_1$-$C_3$) aliphatic chlorides and ($C_2$-$C_8$) aliphatic ethers.

18. The preparation process according to claim 1, wherein the salt of one of the substantially pure enantiomers of the racemic compound of formula (I) is obtained directly from the reaction medium by treatment with an alkaline metal salt or alkaline earth metal salt.

19. The preparation process according to claim 18, wherein the alkaline metal or alkaline earth metal salt is an alkaline metal or alkaline earth metal halide.

20. The preparation process according to claim 19, wherein the alkaline metal or alkaline earth metal halide is magnesium chloride.

* * * * *